(12) United States Patent
Cho

(10) Patent No.: US 8,886,505 B2
(45) Date of Patent: Nov. 11, 2014

(54) METHOD OF PREDICTING PROTEIN-LIGAND DOCKING STRUCTURE BASED ON QUANTUM MECHANICAL SCORING

(75) Inventor: Art Eunsung Cho, Seoul (KR)

(73) Assignee: Quantum Bio Solutions Co., Ltd., Seoul (KR)

( * ) Notice: Subject to any disclaimer, the term of this patent is extended or adjusted under 35 U.S.C. 154(b) by 286 days.

(21) Appl. No.: 12/846,394

(22) Filed: Jul. 29, 2010

(65) Prior Publication Data

US 2011/0246166 A1    Oct. 6, 2011

(30) Foreign Application Priority Data

Mar. 31, 2010    (KR) .................. 10-2010-0029597

(51) Int. Cl.
| | |
|---|---|
| G01N 33/48 | (2006.01) |
| G01N 33/50 | (2006.01) |
| G06F 19/16 | (2011.01) |
| G06F 19/12 | (2011.01) |
| G06F 19/10 | (2011.01) |

(52) U.S. Cl.
CPC ............... *G06F 19/16* (2013.01); *G06F 19/12* (2013.01); *G06F 19/10* (2013.01)
USPC .............................................. 703/11; 702/19

(58) Field of Classification Search
CPC .......... G06F 19/10; G06F 19/12; G06F 19/16
USPC .............................................. 702/19; 703/11
See application file for complete search history.

(56) References Cited

PUBLICATIONS

Cho et al. Journal of Computational Chemistry, vol. 26, Issue 9, 915-931, 2005.*
QSite 5.0 User Manual, 2008, pp. 1-70.*
Murphy et al. Journal of Computational Chemistry, vol. 21, No. 16, 1442-1457, 2000.*
Art E. Cho, et al., "Extension of QM/MM Docking and its Applications to Metalloproteins", The Journal of Computational Chemistry, 2009, pp. 2609-2616, vol. 30, No. 16.
Art E. Cho et al., "Quantum Mechanical Scoring for Protein Docking", The Journal of Chemical Physics, 2009, pp. 134108-1-134108-6, vol. 131.
Emanuele Perola et al., "A Detailed Comparison of Current Docking and Scoring Methods on Systems of Pharmaceutical Relevance", Proteins: Structure, Function and Bioinformatics, 2004, pp. 235-249, vol. 56.

* cited by examiner

*Primary Examiner* — Michael Borin
(74) *Attorney, Agent, or Firm* — Sughrue Mion, PLLC

(57) ABSTRACT

Provided is a protein-ligand docking prediction method based on quantum mechanical scoring. The method includes evaluating a protein-ligand docking structure by using a molecular mechanical energy-based scoring function and reevaluating the protein-ligand docking structure by using a rescoring function obtained by combining a quantum mechanical factor with the molecular mechanical energy-based scoring function. In accordance with the method using the quantum mechanical scoring, it is possible to more accurately carry out modeling than conventional force field-based methods.

5 Claims, 5 Drawing Sheets
(1 of 5 Drawing Sheet(s) Filed in Color)

METHOD OF PREDICTING PROTEIN-LIGAND DOCKING STRUCTURE BASED ON QUANTUM MECHANICAL SCORING

CROSS-REFERENCE TO RELATED APPLICATION

This application claims the benefit of Korean Patent Application No. 10-2010-0029597 filed on Mar. 31, 2010, the entire disclosures of which are incorporated herein by reference.

FIELD OF THE INVENTION

The present disclosure relates to a method of predicting a protein-ligand docking structure based on quantum mechanical scoring.

BACKGROUND OF THE INVENTION

Protein docking algorithms are designed to simulate interactions between proteins and small molecules to thereby predict bound conformation of protein-ligand complexes. Usually, docking programs are used to determine binding modes of inhibitors bound to active sites of enzymes. Given a protein structure, docking can be a powerful tool for screening compounds and has become an essential component in the field of computer-aided drug design.

A simulation of the binding phenomena of proteins and ligands requires two main components. A conformational search, with which one scans the conformational space of protein-ligand complex, encompasses a great number of algorithms that have been implemented in docking programs over the years. Examples are fast shape matching, genetic algorithms, simulated annealing, and Monte Carlo simulations. The other component of docking is scoring that scores protein-ligand binding structures in order of possibility. For the scoring, detailed description of atomic interactions between a protein and a ligand is needed. The scoring usually uses force field-based molecular mechanical calculations with some auxiliary scoring components to rank the generated poses. Scoring can be divided into three categories: empirical, knowledge-based, and physics-based. Among these, the physics-based scoring uses energy functions as a main component. However, this energy function is primarily based on a force field and thus cannot take into account of quantum effects. There are some instances for which accounting for quantum effect in docking might be important; one may be a case when electron transfer takes place. There are numerous examples among biological processes in which this phenomenon can be observed. In metalloproteins, charge transfer could occur between ligand and metal atoms as well as between protein and metal atoms. Therefore, it seems necessary to incorporate quantum mechanical (QM) calculations in docking for these proteins.

Hybrid quantum mechanical/molecular mechanical (QM/MM) methods have become a standard tool for the description of large molecular systems, in which QM level calculations are needed for parts of the system. A typical example of such systems can be an enzyme, since it is a large biomolecule but a small region thereof is involved in catalytic activities. All QM/MM methods are developed to treat quantum mechanically the part of the system that undergoes the most important electronic changes during a reaction or upon binding a substrate and the rest of the system by molecular mechanics.

BRIEF SUMMARY OF THE INVENTION

The present inventors have conceived the present invention by conducting a study for the use of QM energy (QM scoring) for docking based on the fact that, in some cases, only QM calculations can describe the binding of a ligand and protein accurately.

Accordingly, in the present disclosure, there is provided a method of predicting a protein-ligand docking structure by using the QM scoring, which is capable of modeling more accurately than conventional force field-based methods.

However, problems to be solved by the present invention are not limited to the above-described problem and other problems which have not been described above can be clearly understood by those skilled in the art by the following descriptions.

As a technical means for solving the above-described technical problem, there is provided a method of predicting a protein-ligand docking structure. The method includes evaluating a protein-ligand docking structure by using a molecular mechanical energy-based scoring function and reevaluating the protein-ligand docking structure by using a rescoring function obtained by combining a quantum mechanical factor with the molecular mechanical energy-based scoring function.

To be more specific, the method includes generating diverse poses by performing force field-based docking with respect to a selected protein-ligand set and selecting the most stable pose by performing a quantum mechanical calculation on a predefined quantum mechanical region with respect to the generated diverse poses and scoring energy values obtained by the quantum mechanical calculation.

In accordance with an example of the present disclosure, by using QM scoring, it is possible to more accurately carry out modeling as compared to conventional force field-based docking methods.

In accordance with an example of the present disclosure, by using QM energy as scoring for selecting a protein-ligand pose, it is possible to accurately and quickly explain a suitable binding mode for a hydrophobic binding site as well as previous problems (a polar binding site and metalloprotein) of QM/MM docking.

In accordance with an example of the present disclosure, it is possible to accurately predict protein-ligand docking without a great increase in computational cost.

Accordingly, a method of predicting a protein-ligand docking structure of the present disclosure can be applied to various fields including the field of computer-aided drug design.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee. The disclosure may best be understood by reference to the following description taken in conjunction with the following figures.

DETAILED DESCRIPTION OF THE INVENTION

Figure 1A:
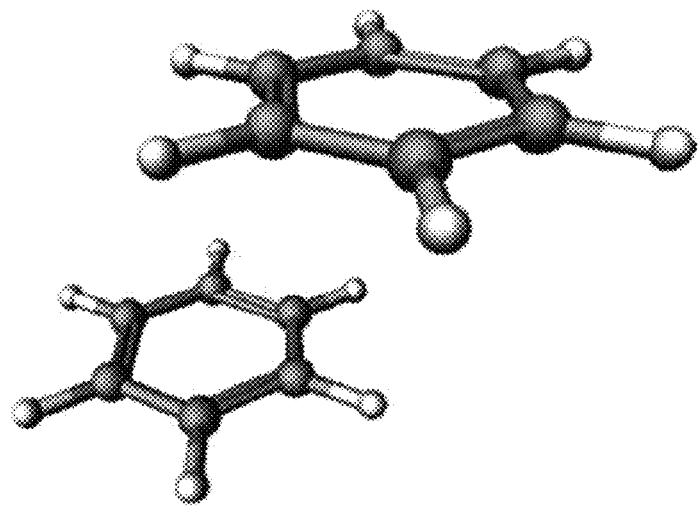
FIG. 1 shows (a) a parallel-displaced configuration and (b) a T-shaped configuration of a benzene dimer.

Hereinafter, embodiments of the present invention will be described in detail with reference to the accompanying drawings.

It will be understood by those skilled in the art that, in general, terms used herein but the following definitions of terms are provided for easy understanding of the present invention. However, if not clearly defined, the terms should be interpreted as meanings accepted by those skilled in the art at that time.

Through the whole document, the term "comprises or includes" and/or "comprising or including" used in the document means that one or more other components, steps, operation and/or existence or addition of elements are not excluded in addition to the described components, steps, operation and/or elements but further included unless stated otherwise.

The terms "about or approximately" or "substantially" are intended to have meanings close to numerical values or ranges specified with an allowable error and intended to prevent accurate or absolute numerical values disclosed for understanding of the present invention from being illegally or unfairly used by any unconscionable third party.

The term "docking" generally refers to a computational simulation on a binding between a receptor (e.g., protein) and a candidate ligand. In the field of molecular modeling, when two molecules are bound to form a stable complex, docking is used as a method for predicting a desirable orientation of a first molecule with respect to a second molecule.

The term "pose" means a candidate binding mode generated by docking.

The term "scoring" refers to, in the fields of computational chemistry and molecular modeling, a process of evaluating a rank of a particular pose generated between two molecules after docking.

In accordance with a first aspect of the present disclosure, there is provided a method of predicting a protein-ligand docking structure. The method includes evaluating a protein-ligand docking structure by using a molecular mechanical energy-based scoring function and reevaluating the protein-ligand docking structure by using a rescoring function obtained by combining a quantum mechanical factor with the molecular mechanical energy-based scoring function.

In one illustrative embodiment, the quantum mechanical factor may be combined with the molecular mechanical energy-based scoring function by defining a site of protein-ligand binding between a protein and a ligand as a quantum mechanical region (QM region) and performing a quantum mechanical calculation on the quantum mechanical region, but the present disclosure is not limited thereto. By way of example, a protein residue within about 5 Å around the ligand and the protein-ligand binding site may be defined as the quantum mechanical region.

In the embodiment, the quantum mechanical region may be variably defined depending on a kind of the protein-ligand binding, but the present disclosure is not limited thereto. By way of example, (i) if the protein-ligand binding is a binding between a metalloprotein and a ligand, the ligand, a metal ion of the metalloprotein, and coordinating protein atoms are defined as the quantum mechanical region; and, (ii) if the protein-ligand binding is hydrophobic, the ligand and the protein atoms within about 5 Å from the protein-ligand binding site are defined as the quantum mechanical region. Further, by way of example, in the hydrophobic binding, if the protein-ligand binding includes a π-stacking interaction, the quantum mechanical region may include the ligand and a residual group of the protein that are capable of having a π-stacking interaction in the protein-ligand binding. Further, (iii) if the protein-ligand binding is polar, the ligand is defined as the quantum mechanical region.

In the embodiment, the rescoring function combined with the quantum mechanical factor is represented by the following equation (1) but not limited thereto:

$$E = E_{QM} + E_{MM} + E_{QM/MM} \quad (1)$$

wherein $E_{QM}$ is a quantum mechanical energy, $E_{MM}$ may be a molecular mechanical energy, and $E_{QM/MM}$ is an interaction energy between a quantum mechanical region and a molecular mechanical region.

Further, the $E_{QM/MM}$ of the equation (1) may be represented by the following equation (2):

$$E_{QM/MM} = E_{Coulomb} + E_{vdW} + E_{QM/MM}^{int.coor} \quad (2)$$

wherein $E_{coulomb}$ is a Coulomb energy, $E_{vdW}$ is a van der Waals energy, and $E_{QM/MM}^{int.coor}$ is an energy due to discrimination between a quantum mechanical region and a molecular mechanical region.

In the embodiment, the method of predicting a protein-ligand docking structure is a physics-based method that does not include an empirical factor, but not limited thereto.

In accordance with a second aspect of the present disclosure, there is provided a method of predicting a protein-ligand docking structure. The method includes generating diverse poses by performing force field-based docking with respect to a selected protein-ligand set and selecting the most stable pose by performing a quantum mechanical calculation on a predefined quantum mechanical region with respect to the generated diverse poses and scoring energy values obtained by the quantum mechanical calculation.

In one illustrative embodiment, generating the diverse poses may include setting a clustering parameter to allow no similar poses to lie within a predetermined range, thereby ensuring diversity in the poses, but the present disclosure is not limited thereto. By way of example, in generation of initial poses, the clustering parameter may be set so that no poses are similar within about 1.5 Å RMSD in coordinates to each other.

In the embodiment, selecting the most stable pose may include shortly repeating a geometry optimization with respect to constrained protein atoms, but the present disclosure is not limited thereto. By way of example, the geometry optimization can be performed five times or less without a great increase in computational cost.

In the embodiment, the predefined quantum mechanical region is a site of protein-ligand binding between a protein and a ligand, and the predefined quantum mechanical region can be variably defined depending on a kind of the protein-ligand binding, but the present disclosure is not limited thereto. By way of example, the binding site defined as the quantum mechanical region can be variably defined depending on the kind of the protein-ligand binding such as a metalloprotein binding, a polar binding, or a hydrophobic binding.

Hereinafter, there will be provided some examples for better understanding of the present disclosure. However, the following examples will be provided for the purpose of illustration, and, thus, the present disclosure is not limited to the examples.

Test Set and Categorization

To validate the above-described method, a variety of target proteins representing three important binding site characterizations was chosen in an example of the present disclosure: polar (P), metal-contained (M), and hydrophobic (H). The list of complexes from the test set of Perola et al. [*Proteins: Struct., Funct., Bioinf.* 56, 235, 2004, the entire disclosures of which are incorporated herein by reference] was shortened by eliminating structures whose resolutions are bigger than about 2.0 Å. Further, using SiteMap of Schrödinger suite and visual inspection, the list was categorized into three groups. SiteMap calculates the hydrophobic and hydrophilic character values. These values were compared and decided whether the binding sites were more hydrophobic than hydrophilic or vice versa. Using a script program, the presence of metal ions within about 7 Å of the center of binding site was determined and labeled those with metal ions as a metal-contained group. Each and every complex was checked visually to confirm that this categorization was reasonable. The structure files of chosen cocrystals were downloaded from the protein data bank (PDB) websites and prepared with the Protein Preparation Wizard of Schrödinger suite for docking. During this preparation, water molecules except for those that are directly involved in interactions with ligands and protein atoms were eliminated. Hydrogens were added to ligands based on Epik calculations for proper pKa values. Energy minimization was performed with fixed heavy atoms to relax the added hydrogens using IMPACT.

Docking Method

For docking, Glide 4.5 was chosen in an example of the present disclosure. Glide was used to generate prediction of poses for a given protein-ligand complex, but also as an initial-pose generating program. QM/MM calculations were performed on the poses that were generated by Glide. For all the docking runs performed for this example, standard Precision (SP) mode of Glide was used. A docking algorithm in Glide utilizes a hierarchical search protocol. In a first stage, about 5000 poses were kept for each ligand docking from initial generation for refinement. After the refinement, about 400 poses was kept for minimization using grids during which a maximum of 100 steps were imposed. Finally, ten poses were scored and ranked after minimizations. Selection of the final ligand pose for Glide is done with GlideScore, which is an extension of an empirically based Chem-Score function of Eldridge et al. Final assessment of ligand pose prediction was done as in most literature by calculating RMSD (root-mean-square-deviation) in coordinates of non-hydrogen ligand atoms from crystal structures. In generation of initial poses for QM/MM calculations, the clustering parameters are set so that no poses are similar within about 1.5 Å RMSD in coordinates to each other. This is to ensure diversity in poses. These parameters were good enough for present examples as there were at least one pose below about 1.0 Å RMSD to crystal structure among ten final poses for each example except for two of them.

QM/MM Calculations

QM/MM calculations were done with QSite 4.0 of Schrödinger suite. QM/MM energy calculated by QSite can be represented as follows:

$E = E_{QM} + E_{MM} + E_{QM/MM}$, where $E_{QM/MM} = E_{Coulomb} + E_{vdW} + E_{QM/MM}^{int.coor}$.

Here the last term in QM/MM energy is due to a boundary treatment of QM and MM regions. If there is no covalent bond between a QM region and a MM region, QM/MM calculations become trivial and it is only a matter of using electrostatic embedding in which QM wave functions are influenced by point charges of MM region. QSite does indeed adopt such scheme. However, if a QM/MM border crosses covalent bonds, QSite uses frozen orbital method for the treatment of such problem. For QM calculations, DFT was used. The calculations for QM part were done with JAGUAR 6.5, which constitutes one arm of QSite. For DFT calculations, 6-31G basis set and B3LYP hybrid functional, a combination of which has been shown to yield excellent results for atomization energies and transition states in a wide range of chemical systems, were adopted for most part. An exception was a hydrophobic group, for which LDA (local density approximation) functional Vosko-Wilk-Nusair was used for the reason that will be explained in detail below.

QM Scoring Protocol

A QM scoring protocol using QM/MM calculations in the present disclosure is akin to basic rescoring schemes that are prevalent in modern virtual screening practice. It is designed to minimize QM level calculations, which can cost large amount of computational time, yet to capture the essential details that only QM calculations can deliver. The key idea is to generate as diverse poses as possible in the initial stage performed with force field-based docking. As was mentioned above, a clustering process was used, in which poses that are close together get eliminated, to span the conformational space as complete as possible. The top ten scoring ligand poses from initial Glide docking were placed in the receptor and QM/MM calculations were performed with varying QM region definition on the complexes. During the QM/MM calculations, a short geometry optimization (up to five iterations) was allowed with all the protein atoms constrained. Although Glide performs postdocking minimization with full van der Waals radii of ligand atoms, QM calculations could still find different local minima than MM based minimization would. Thus to find locally accessible QM potential energy surface minima, this process was carried out. However, allowing geometry optimization with QM/MM exacerbates the computational cost. The present inventors' compromise was to limit this step to a small number. After the QM/MM calculations, the QM/MM energy values were then compared and the pose with the lowest energy was picked as the top scoring one. The variation in the definition of QM region was invoked by carrying out calculations on two kinds of models: one with only ligands as a QM region and the other with surrounding protein atoms and ligands as a QM region. The significance of this variation can be comprehended in two ways. One is the consideration of computational cost. The increase in the number of atoms (therefore number of electrons) will significantly affect the computational time. It is a practical interest that one should try to reduce the number of atoms in QM region as much as possible. On the other hand, in order to describe the ligand binding accurately, one has to include all the atoms that are involved in the essential interactions. The present disclosure is provided to find a balance between these two premises by experimenting both variations of a QM region on different groups of examples.

Results and Discussion

I. Illustration of the Method

Table 1 below demonstrates how the QM scoring with QM/MM energy calculations works for the case of 1MQ5, a human factor Xa complex.

TABLE 1

Redocked poses of 1MQ5 generated by Glide SP and
rescored by QM/MM energy (QM regions are defined
to include just the ligands.).

| Rank by Glide SP | GlideScore | RMSD Glide SP | RMSD after QM/MM | Relative QM/MM energy (kcal/mol) |
|---|---|---|---|---|
| Native | −8.52 | 0.00 | 0.02 | 0.00 |
| 1 | −9.08 | 1.73 | 1.75 | 56.75 |
| 2 | −8.58 | 2.20 | 2.22 | 81.88 |
| 3 | −7.45 | 0.44 | 0.43 | 30.58 |
| 4 | −7.92 | 2.39 | 2.37 | 146.97 |
| 5 | −7.12 | 2.02 | 2.04 | 87.50 |
| 6 | −6.12 | 3.20 | 3.25 | 131.62 |
| 7 | −6.07 | 2.89 | 2.94 | 124.54 |
| 8 | −4.78 | 6.10 | 6.08 | 116.28 |
| 9 | −4.58 | 6.73 | 6.75 | 112.73 |
| 10 | −4.37 | 3.75 | 3.77 | 148.77 |

In this example, the QM/MM energy of a native pose was set to 0 and all the other energies were recalculated relatively. As seen from Table 1, the QM/MM energy of the native pose was the lowest. This is a good indication that the QM/MM energy can accurately describe a binding mode of the example at hand. On the contrary, GlideScore was not the lowest for the native pose. The second lowest energy pose with the QM/MM energy was the one that is closest to the native structure among all the Glide generated poses with RMSD of about 0.43 Å. This would be the prediction by QM scoring protocol for the best scoring one. The pose predicted by Glide had RMSD of about 1.73 Å, which is acceptable, but the QM scoring performed better in this case.

II. Application to Polar and Metal-Contained Groups

The same procedure was used for the rest of the test cases. The complete result is summarized in Table 2 below.

TABLE 2

Complete result of comparison redocking with
Glide, QM/MM docking with only ligands only in a QM region,
and QM/MM docking with ligands and binding site protein
residues in a QM region. Values shown are RMSD from crystal
structures of the best scoring poses predicted by each
method.

| | PDB ID | Best pose by Glide | Best pose by QM/MM energy Ligand only | Protein atoms included |
|---|---|---|---|---|
| Polar group | 1AOE | 0.73 | 0.71 | 0.70 |
| | 1BKM | 1.62 | 0.96 | 0.95 |
| | 1CET | 3.65 | 0.85 | 0.86 |
| | 1D3P | 3.14 | 1.48 | 1.46 |
| | 1D4P | 0.79 | 0.77 | 0.77 |
| | 1H1P | 4.77 | 4.76 | 4.78 |
| | 1HPV | 0.87 | 0.86 | 0.87 |
| | 1K7F | 1.63 | 1.08 | 1.07 |
| | 1MQ5 | 1.73 | 0.43 | 0.44 |
| | 1MQ6 | 1.45 | 1.42 | 1.15 |
| | 1NHU | 5.27 | 1.54 | 1.54 |
| | 1OHR | 0.43 | 0.43 | 0.44 |
| | 1QPE | 6.35 | 3.41 | 3.42 |
| | 1SYN | 3.59 | 1.84 | 1.83 |
| | 2QWI | 1.25 | 0.85 | 0.75 |
| | 3ERK | 1.13 | 0.75 | 0.75 |
| | 3ERT | 0.76 | 0.79 | 0.75 |
| | 5STD | 0.38 | 0.36 | 0.37 |
| Metal-contained group | 1ATL | 3.43 | 3.04 | 0.89 |
| | 1AZM | 2.33 | 1.31 | 1.31 |
| | 1CIM | 0.95 | 1.26 | 1.26 |
| | 1G4O | 2.98 | 4.53 | 1.32 |
| | 1HFC | 2.31 | 1.04 | 1.02 |
| | 1I8Z | 2.50 | 4.60 | 1.88 |
| | 1IF7 | 2.54 | 2.09 | 1.24 |
| | 1MMB | 2.31 | 2.31 | 1.45 |
| | 1MNC | 0.45 | 0.47 | 0.44 |
| | 1THL | 7.91 | 1.23 | 1.45 |
| | 3CPA | 3.15 | 2.80 | 2.61 |
| | 3TMN | 7.98 | 3.07 | 1.56 |
| | 830C | 0.33 | 0.31 | 0.34 |
| | 966C | 0.65 | 0.64 | 0.63 |
| Hydrophobic group | 13GS | 1.16 | 1.14 | 1.15 |
| | 1D6V | 4.09 | 4.06 | 1.89 |
| | 1ELA | 2.03 | 2.05 | 1.98 |
| | 1F0T | 0.33 | 1.18 | 1.15 |
| | 1F4E | 1.75 | 1.51 | 1.27 |
| | 1F4F | 2.91 | 2.44 | 1.50 |
| | 1FCX | 0.62 | 0.64 | 0.60 |
| | 1FCZ | 0.24 | 0.23 | 0.25 |
| | 1FJS | 2.27 | 2.36 | 1.85 |
| | 1K22 | 2.15 | 1.98 | 0.98 |
| | 1L2S | 2.26 | 2.26 | 1.09 |
| | 1M48 | 2.22 | 2.12 | 0.81 |

For a P group, defining just the ligands as a QM region worked rather well and extending the definition of a QM region to include the surrounding protein atoms did little. The prediction of poses that are about 2.0 Å or lower in RMSD to the crystal structures was achieved in all but 2 out of 20 cases with both definitions of a QM region. Those two cases which failed were the ones in which the initial Glide docking could not find any pose under about 2.0 Å RMSD among ten top rankers. To confirm that the failure were not due to scoring error but rather sampling error, QM/MM energy calculations were carried out on the native poses for these cases. Table 3 shows the QM/MM energy of native poses calculated relatively to the energy of the predicted best poses of 1H1P and 1QPE.

TABLE 3

QM/MM energy of native pose calculated relatively
to the energy of the pose with the lowest energy for 1H1P
and 1QPE (QM region definition is done in two ways: ligand
only and protein atoms included.).

| | QM/MM energy of native pose (kcal/mol) | |
|---|---|---|
| PDB ID | Ligand only | Protein atoms included |
| 1H1P | −76.31 | −81.64 |
| 1QPE | −141.38 | −132.89 |

This information does not guarantee that the native poses are at the global minima of QM/MM energy surface; however, in the examples, for those for which good poses could not be found, the native pose QM/MM energies were significantly lower, suggesting that with better sampling, the chance of finding poses that are close to the native ones is high. On the other hand, for a M group, the definition of a QM region should include ligands, metal ions, and coordinating protein atoms to obtain substantially better results than regular Glide docking. With only ligands as a QM region, a QM scoring protocol failed to predict poses that are under about 2.0 Å RMSD in seven cases, whereas when metal ions and coordinating protein atoms were included as well, the failure was reduced to only one case. This result is in accord with the present inventors' previous research [A. E. CHO, D. Rinaldo, "Extension of QM/MM Docking and its Applications to Metalloprotein" J. Comput. Chem. 30: 2609-2616, 2009, the entire disclosures of which are incorporated herein by reference] with metalloprotein and a QM/MM docking protocol. In that research, it was shown that force field based model cannot accurately describe the charge distribution between a metal ion and surrounding protein atoms/ligand atoms. It was necessary to include all these atoms in QM region to find a correct binding mode.

III. Hydrophobic Group and π-Stacking

Figure 1B:
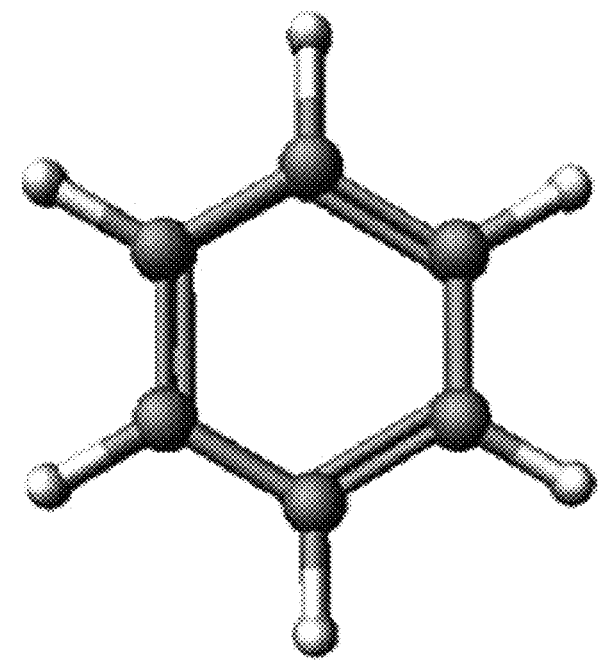
Figure 1B:
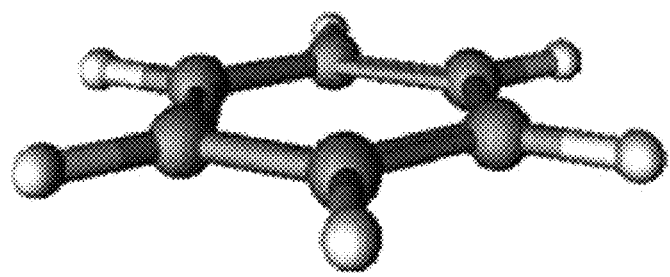
Figure 2A:
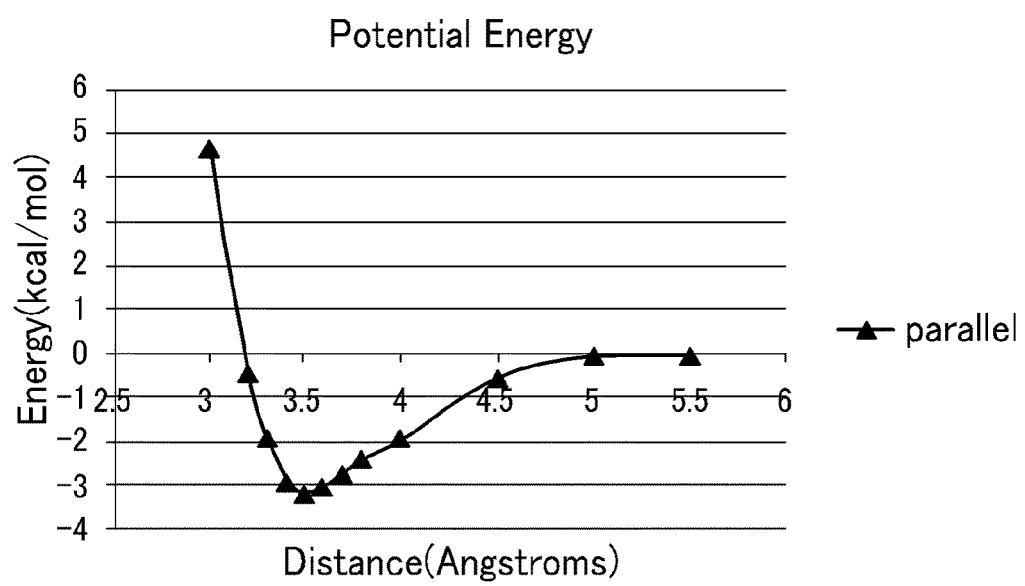
FIG. 2 provides graphs showing potential energy as a function of vertical distance between two benzene rings in (a) a parallel-displaced configuration and (b) a T-shaped configuration, wherein in parallel-displaced configuration, $R_2$ is fixed at 1.5 Å, which gives a close to maximum binding energy.
Figure 2B:
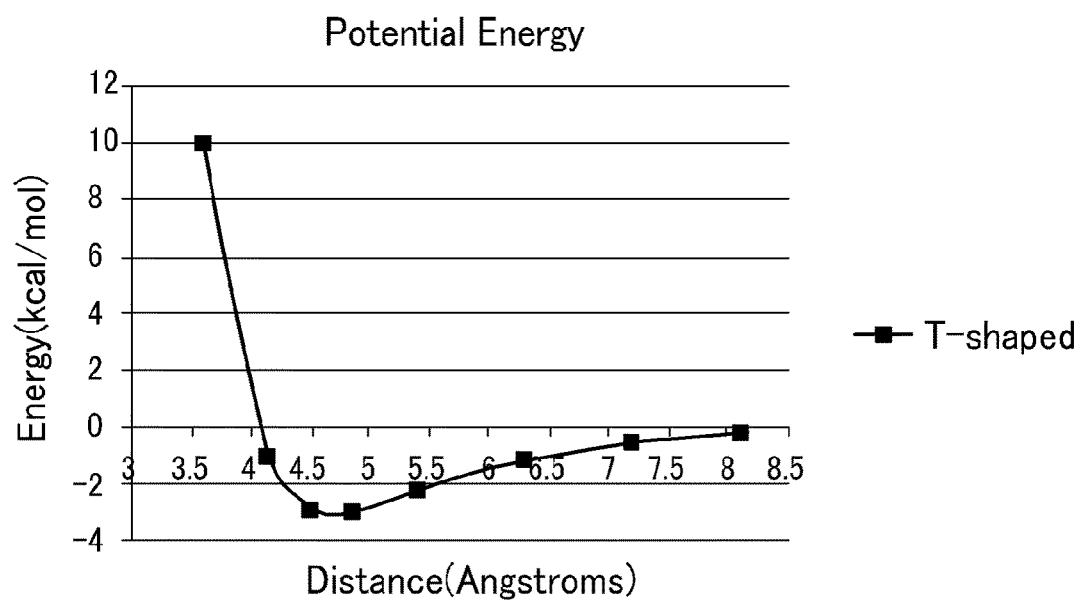
Figure 3:
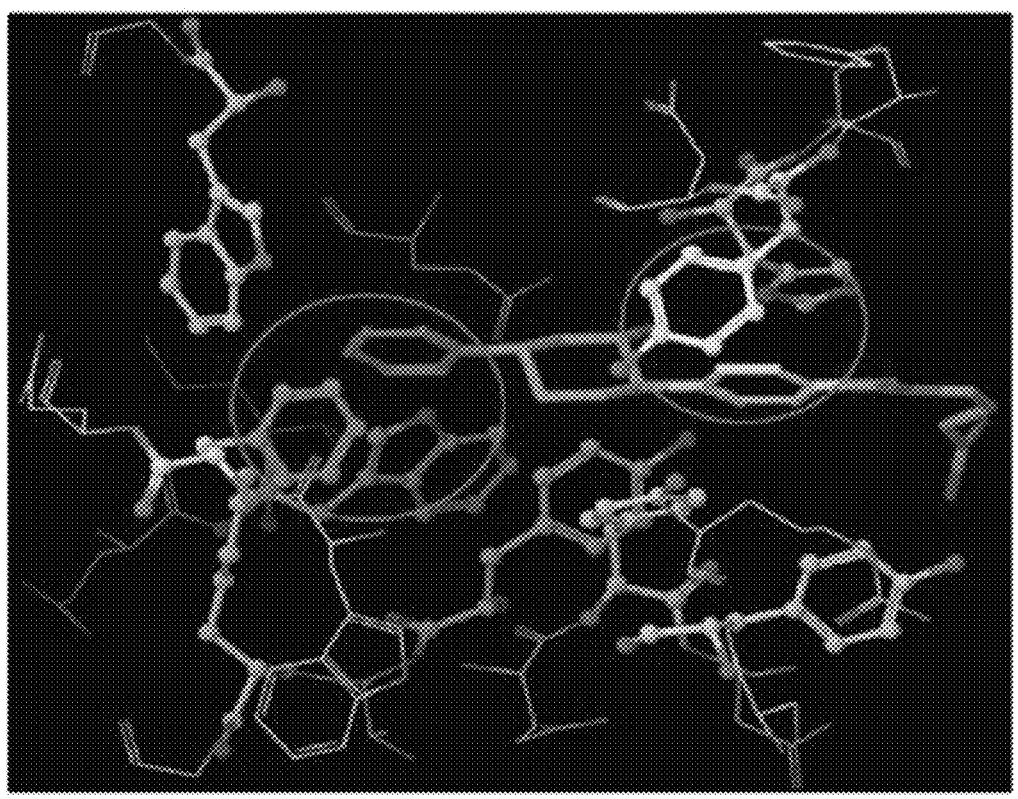
FIG. 3 shows a binding site of 1D6V wherein residues with ball and stick representation and ligands are included in a QM region and purple and yellow colored rings (circled in red) are possible partners of π-π stacking interactions.

A hydrophobic (H) group presents an interesting picture. It was noted in the present inventors' previous research that employing QM/MM calculations to rescale the atomic charges for hydrophobic binding sites does not yield any appreciable improvement since hydrophobic groups are not polarized much upon ligand binding. On the other hand, it was found in other research that with careful molecular dynamics analysis, one can devise a geometric motif to describe ligand binding in hydrophobic sites. The proposed motif-based scoring addresses the geometric motifs, which can be interpreted as having π-π stacking interactions. In the present disclosure, some of the hydrophobic group examples have similar motifs as the ones described in that research. The present inventors attempted to model such motifs with QM/MM calculations. In doing so, however, the present inventors had to address an important issue. It has been known that DFT calculations with popular functions such as B3LYP without London-dispersion correction are incapable of predicting bound states of π-stacking configurations. Surprisingly however, it was reported that LDA performs fairly well in description of π-stacking structures. In order to verify the relevance of use of DFT that is readily available, some simple calculations were run by using benzene dimer in parallel-displaced and T-shaped configurations (see FIG. 1A, 1B). FIG. 2A and FIG. 2B show the DFT energies as a function of vertical separation of two benzene rings in these two configurations. A moderate combination of 6-31G basis set and Slater-Vosko-Wilk-Nusair functional were used. Binding energies found from these curves were about 3.2 kcal/mol and about 3.0 kcal/mol for parallel-displaced and T-shaped configurations, respectively. These values are overestimation of the binding energies of π-stacking configurations as compared with those that can be found in other literature by a slight amount, but nonetheless give qualitatively correct picture of bound states of them. Although LDA has limitation in description of other phenomena, the above-described simple test shows that it can be used to model π-stacking. For a H group, QM/MM calculations with ligands only as a QM region did not change much of the result of regular Glide. However, when there were included the residues that have possible π-stacking interactions with functional groups of ligands as in FIG. 3, the prediction improved by a substantial amount as the method of the present disclosure failed to give poses that are under about 2.0 Å for none of the H groups.

IV. Comparison with Force Field-Base Rescoring Scheme

QM scoring of the present disclosure relies completely on a physics-based energy function. The question is how a force field energy function can fare as scoring for docking in comparison. The answer to this question could validate practicality and justification for use of QM scoring even though its computational cost is much higher than force field-based methods. For a typical sized (from about 50 atoms to about 100 atoms) ligand, force field energy calculations take a fraction of a minute, while QM energy calculations can take in the order of tens of minutes. OPLS 2005 as implemented in IMPACT19 molecular modeling software was used to calculate force field-based binding energy of those cases for which GlideScore failed to predict a good pose but QM scoring succeeded. For this experiment, ten ranked poses were taken along with the native pose of two examples in each of three groups and calculated binding energies as follows. Although the postdocking minimization option in Glide was adopted, since GlideScore includes empirical terms on top of force field based MM energy, the poses predicted by Glide might not be at local minima on pure OPLS force field potential energy surface. Thus, each pose was minimized with protein fixed by OPLS force field energy. For native poses, for which the binding energy was evaluated in order to check whether or not force field energy function gives minima at such configurations, the minimization was limited to RMSD change of about 0.2 Å. For poses generated by docking, RMSDs from crystal structures were checked when minimization was done since the conformation of these poses could change by an extended amount. After minimization was done, the single point energy was evaluated and, by subtracting receptor-alone and free ligand energies, binding energy was computed. Table 4 shows the result of force field rescoring experiment.

TABLE 4

Result of OPLS 2005 force field based rescoring with energies in kcal/mol.

|  |  | Binding energy of native pose | Binding energy of best scoring pose | RMSD of best scoring pose |
|---|---|---|---|---|
| Polar | 1CET | −36.0 | −42.1 | 4.48 |
|  | 1D3P | −32.7 | −110.8 | 2.52 |
| Metal | 1G4O | −74.4 | −84.4 | 3.69 |
|  | 1IF7 | −68.8 | −99.6 | 3.08 |
| Hydrophobic | 1D6V | −17.0 | −160.0 | 3.36 |
|  | 1F4F | −200.6 | −286.2 | 2.06 |

Force field rescoring could predict poses under about 2 Å in none of the six cases. In fact, the present inventors found that none of the native poses scored the lowest energy. This result is not surprising in that although GlideScore features empirical parameters, the main component is still force field-based energies. For the cases examined, only QM energy could give the right scoring for docking.

In the present disclosure, the present inventors have demonstrated the possibility of using QM energy as scoring for protein-ligand pose selection. In addition to the previously tackled problems with QM/MM docking (polar binding sites and metalloproteins), the present inventors have shown that for hydrophobic binding sites, QM energy can describe the right binding mode with π-π interaction motifs. Such cases would be difficult to accurately model using conventional docking methods as well as previous versions of QM/MM docking in which QM calculations are only fitted to rescale atomic charges. For accurate description of protein-ligand interactions for which π-stacking serves as the main factor and is ubiquitous in hydrophobic binding sites, a QM energy with the right kind of theory can be used as scoring. In order to utilize this QM/MM energy for prediction of binding affinity, however, one must rescale the energy values. Total QM/MM energy includes, on top of MM-based energies, nuclear and electron energies, which contribute to greater differentials between different poses.

Although the present disclosure have been described with the above-described examples, it would be understood by those skilled in the art that various changes and modifications may be made without changing technical conception and essential features described in the claims of the present disclosure.

What is claimed is:

1. A computer-implemented method of predicting a protein-ligand docking structure, the method comprising:

evaluating with a computer a protein-ligand docking structure by using a molecular mechanical energy-based scoring function; and reevaluating with said computer the protein-ligand docking structure by using a rescoring function obtained by incorporating a quantum mechanical factor with the molecular mechanical energy-based scoring function, selecting a most stable pose by performing a quantum mechanical calculation on a predefined quantum mechanical region with respect to the generated diverse poses and scoring energy values obtained by the quantum mechanical calculation, thereby predicting the protein-ligand docking structure, wherein the rescoring function obtained by incorporating the quantum mechanical factor is represented by the following equation (1):

$$E = E_{QM} + E_{MM} + E_{QM/MM} \quad (1)$$

wherein $E_{QM}$ is a quantum mechanical energy,
$E_{MM}$ is a molecular mechanical energy,
$E_{QM/MM}$ is an interaction energy between a quantum mechanical region and a molecular mechanical region and is represented by the following equation (2):

$$E_{QM/MM} = E_{Coulomb} + E_{vdW} + E_{QM/MM}^{int.coor} \quad (2)$$

wherein $E_{coulomb}$ is a Coulomb energy, $E_{vdW}$ is a van der Waals energy, and $E_{QM/MM}^{int.corr}$ is an energy due to discrimination between a quantum mechanical region and a molecular mechanical region, and wherein the protein-ligand binding is hydrophobic binding that includes a π-stacking interaction, and wherein the ligand atoms and protein atoms of protein residues within 5 Å from the protein-ligand binding site are defined as the quantum mechanical region.

2. The method of claim 1, wherein the quantum mechanical factor is combined with the molecular mechanical energy-based scoring function by defining a site of protein-ligand binding between a protein and a ligand as a quantum mechanical region (QM region) and performing a quantum mechanical calculation on the quantum mechanical region.

3. The method of claim 1, wherein evaluating a protein-ligand docking structure includes:

generating diverse poses by performing force field-based docking with respect to a selected protein-ligand set.

4. The method of claim 3, wherein generating the diverse poses includes:

setting a clustering parameter to allow no similar poses to lie within a predetermined range, thereby ensuring diversity in the poses.

5. The method of claim 1, wherein selecting the most stable pose includes:

performing a geometry optimization five times or less with respect to a constrained protein atom.

* * * * *